United States Patent
Arai et al.

(10) Patent No.: US 9,649,322 B2
(45) Date of Patent: May 16, 2017

(54) SPHINGOMYELIN-CONTAINING SUPPLEMENT

(71) Applicant: KAO CORPORATION, Chuo-ku (JP)

(72) Inventors: Youichi Arai, Sumida-ku (JP); Yuki Ishida, Sumida-ku (JP); Yasushi Shioya, Sumida-ku (JP)

(73) Assignee: KAO CORPORATION, Chuo-ku (JP)

( * ) Notice: Subject to any disclaimer, the term of this patent is extended or adjusted under 35 U.S.C. 154(b) by 0 days.

(21) Appl. No.: 14/654,733

(22) PCT Filed: Dec. 27, 2013

(86) PCT No.: PCT/JP2013/085161
§ 371 (c)(1),
(2) Date: Jun. 22, 2015

(87) PCT Pub. No.: WO2014/104316
PCT Pub. Date: Jul. 3, 2014

(65) Prior Publication Data
US 2015/0342971 A1    Dec. 3, 2015

(30) Foreign Application Priority Data

Dec. 28, 2012  (JP) .................................. 2012-288219

(51) Int. Cl.
    A61K 9/20       (2006.01)
    A61K 31/683     (2006.01)
    A61K 31/688     (2006.01)
    A23L 33/10      (2016.01)
    A23L 33/115     (2016.01)
    A61K 9/00       (2006.01)

(52) U.S. Cl.
    CPC ............ *A61K 31/683* (2013.01); *A23L 33/10* (2016.08); *A23L 33/115* (2016.08); *A61K 9/2013* (2013.01); *A61K 9/2018* (2013.01); *A61K 31/688* (2013.01); *A61K 9/0056* (2013.01)

(58) Field of Classification Search
    CPC ....... A61K 9/20; A61K 9/2013; A61K 9/2018
    See application file for complete search history.

(56) References Cited

U.S. PATENT DOCUMENTS

| | | | |
|---|---|---|---|
| 6,441,050 B1 * | 8/2002 | Chopra ................ | A61K 9/0095 424/439 |
| 8,268,360 B2 * | 9/2012 | Ota ...................... | A61K 38/011 424/520 |
| 8,486,916 B2 | 7/2013 | Kato et al. | |
| 8,921,342 B2 | 12/2014 | Isogai et al. | |
| 2005/0070877 A1 | 3/2005 | Dobbie | |
| 2006/0280779 A1 | 12/2006 | Burling et al. | |
| 2009/0123630 A1 | 5/2009 | Burling et al. | |
| 2009/0197944 A1 | 8/2009 | Ota et al. | |
| 2010/0048928 A1 | 2/2010 | Kato et al. | |
| 2010/0151037 A1 | 6/2010 | Jiang et al. | |
| 2010/0197638 A1 | 8/2010 | Kato et al. | |
| 2010/0279985 A1 | 11/2010 | Isogai et al. | |
| 2012/0052129 A1 | 3/2012 | Ota et al. | |
| 2012/0208783 A1 | 8/2012 | Kato et al. | |
| 2013/0079307 A1 | 3/2013 | Kato et al. | |
| 2013/0225526 A1 | 8/2013 | Kato et al. | |
| 2013/0252923 A1 | 9/2013 | Kato et al. | |

FOREIGN PATENT DOCUMENTS

| | | |
|---|---|---|
| JP | 2000 139410 | 5/2000 |
| JP | 2003 146883 | 5/2003 |
| JP | 2004 155682 | 6/2004 |
| JP | 2007 112793 | 5/2007 |
| JP | 2007 246404 | 9/2007 |
| JP | 2008 031148 | 2/2008 |
| JP | 2008 184428 | 8/2008 |
| JP | 2009 107987 | 5/2009 |
| JP | 2009 167646 | 7/2009 |
| JP | 2010 59155 | 3/2010 |
| JP | 2010 111608 | 5/2010 |
| JP | 2012 61012 | 3/2012 |
| WO | WO 02/38575 A1 | 5/2002 |
| WO | WO 2006/114790 A2 | 11/2006 |
| WO | WO 2006/114790 A3 | 11/2006 |
| WO | WO 2006/128465 A1 | 12/2006 |

OTHER PUBLICATIONS

Vanderghem et al. Biotechnol. Agron. Soc. Environ., 2010, vol. 14, No. 3, pp. 485-500.*
International Search Report Issued Feb. 10, 2014 in PCT/JP2013/085161 filed Dec. 27, 2013.
Ramstedt, B. et al., "Analysis of natural and synthetic sphingomyelines using high-performance thin-layer chromatography", Eur. J. Biochem., vol. 266, No. 3, pp. 997-1002 , 1999.
Extended European Search Report issued Sep. 29, 2016 in Patent Application No. 13868727.2.

* cited by examiner

*Primary Examiner* — Samira Jean-Louis
(74) *Attorney, Agent, or Firm* — Oblon, McClelland, Maier & Neustadt, L.L.P.

(57) ABSTRACT

A solid supplement comprising the following components (A) and (B):
  (A) sphingomyelin in an amount of from 0.15 to 7% by mass; and
  (B) phosphatidyl inositol or a salt thereof, wherein the mass ratio of the content of phosphatidyl inositol or the salt thereof (B) in terms of phosphatidyl inositol content to the content of sphingomyelin (A) in the solid supplement, i.e., [(B)/(A)], is from 0.05 to 3.

19 Claims, No Drawings

SPHINGOMYELIN-CONTAINING SUPPLEMENT

FIELD OF THE INVENTION

The present invention relates to a sphingomyelin-containing solid supplement.

BACKGROUND OF THE INVENTION

Sphingomyelins are compounds having a structure wherein a phosphocholine is bonded to a ceramide backbone composed of a sphingoid base and a fatty acid, and is known to be abundant in the cell membrane, brain and neural tissue in the body.

Recently, sphingomyelins have been reported to have physiological functions such as an effect of preventing and/or treating dysmnesia (Patent Literature 1), an effect of improving learning ability (Patent Literature 2) and an effect of promoting sialomucin secretion (Patent Literature 3), suggesting a wide range of potential applications, such as application to foods and drinks, especially supplements.

Solid supplements, among formulations, are a commonly preferred dosage form due to their superior handleability and preservability, and ease of consumption. They are generally manufactured through compression molding of raw material powders and additives using a tablet press or the like.

The tableting process may involve tableting problems, such as capping in which part of a supplement facing the upper punch is detached in a cap-form, and sticking in which a portion of the raw material powder or the like is adhered to a punch, leaving defects on the tablet surface. In an attempt to prevent those tableting problems, a lubricant is typically added to the formulation. As such lubricants, sucrose fatty acid esters, lecithin, stearates, talc and the like are widely used (Patent Literatures 4 and 5).
(Patent Literature 1) JP-A-2003-146883
(Patent Literature 2) JP-A-2007-246404
(Patent Literature 3) JP-A-2007-112793
(Patent Literature 4) JP-A-2000-139410
(Patent Literature 5) JP-A-2004-155682

SUMMARY OF THE INVENTION

The present invention provides a solid supplement comprising the following components (A) and (B):

(A) a sphingomyelin in an amount of from 0.15 to 7% by mass; and (B) a phosphatidyl inositol or a salt thereof, wherein the mass ratio of the content of phosphatidyl inositol or the salt thereof (B) in terms of phosphatidyl inositol content to the content of sphingomyelin (A) in the solid supplement, i.e., [(B)/(A)], is from 0.05 to 3.

DETAILED DESCRIPTION OF THE INVENTION

Sphingomyelin-containing supplements, currently on the market, comprise very low concentrations of sphingomyelin, but solid supplements comprising a higher concentration of sphingomyelin will have an advantage in exerting physiological functions of sphingomyelin.

When the present inventors attempted to prepare supplements with a high sphingomyelin content in the form of tablets, however, they found that sphingomyelin had poor tabletability, and that even with widely used lubricants, the tableting problems could occur. In some cases, a rough texture or oil-like flavor was also found to result, which was sensed when a tablet was taken.

Consequently, the present invention relates to providing a solid supplement comprising a large amount of sphingomyelin while exhibiting good manufacturability and excellent feeling sensed when the supplement is taken.

After extensive investigation to solve the above-described problems, the present inventors found that addition of phosphatidyl inositol within a certain range can reduce the problems associated with manufacturing, and can make a solid supplement with reduced roughness of the texture, a reduced oily smell and excellent feeling sensed when the supplement is taken.

The present invention can provide the solid supplement comprising a large amount of sphingomyelin while exhibiting good manufacturability, excellent mouthfeel and flavor, and ease of consumption.

Sphingomyelin (A), used in the present invention, is a compound having a structure wherein a phosphocholine is bonded to a ceramide backbone composed of sphingoid base and a fatty acid. Examples of the fatty acid constituents of sphingomyelin include fatty acids with a saturated or unsaturated linear hydrocarbon chain.

For manufacturability, the percentage of palmitic acid in the total fatty acid constituent of sphingomyelin is preferably 50% by mass (hereafter simply referred to as "%") or less, more preferably 40% or less, even more preferably 30% or less, even more preferably 20% or less. For the same reason, the percentage is preferably 1% or more, more preferably 2% or more, even more preferably 5% or more, even more preferably 10% or more. Hence, the percentage ranges preferably from 1 to 50%, more preferably from 2 to 40%, even more preferably from 3 to 30%, even more preferably from 5 to 20%, even more preferably from 10 to 20%.

Either chemically synthesized or naturally occurring sphingomyelin may be used. There are known methods for chemical synthesis of sphingomyelin which, for example, involves converting ceramide into sphingomyelin by introducing phosphocholine into the hydroxyl group at position 1 of the ceramide via 1) a phosphoramidite intermediate (Weis, Chem Phys Lip, 3, 1999), 2) a cyclic phosphate intermediate (Dong, Tetrahedron Lett, 5291, 1991) or 3) a cyclic phosphite intermediate (Byun, J Org Chem, 6495, 1994).

Highly pure sphingomyelin may also be obtained by purification from cow's milk-derived lipid components using techniques such as dialysis, ammonium sulfate fractionation, gel filtration, isoelectric precipitation, ion exchange chromatography and solvent fractionation (Sanchez-Juanes, Int Dairy J, 273, 2009).

Commercial products of sphingomyelin may also be used.

The content of sphingomyelin (A) in the solid supplement according to the present invention is 0.15 to 7%. In order to achieve the amount of consumption which allows effective exertion of its physiological effects, and set a single dose at a small but effective amount in view of its dosage form, the content of sphingomyelin (A) is preferably 0.2% or more, more preferably 0.3% or more, even more preferably 0.5% or more. In order to maintain the shape of the supplement, the content is preferably 6% or less, more preferably 5% or less, even more preferably 3% or less. Hence, the content ranges preferably from 0.2 to 6%, more preferably from 0.3 to 5%, even more preferably from 0.5 to 3%.

The content of sphingomyelin (A) in the solid supplement can be determined by extracting it from the sample (e.g., W. W. Christie, Lipid Analysis 2nd Edition, p 22-23 (1982)) and then performing thin-layer chromatography (Section 4.3.3.1: RINSHISHITSU SOSEI (HAKUSOU KUROMATOGURAFU HOU) (an English translation of the Japanese title: "Phospholipid Composition (thin-layer chromatography)") in Standard Methods for the Analysis of Fats, Oils and Related Materials, edited by the Japan Oil Chemists' Society (corporate juridical person), published in 2003).

Phosphatidyl inositol (B), used in the present invention, is an acidic phospholipid having inositol as a polar group, and is a constituent of the cell membrane, Golgi membranes, endosomes and the like. Examples of the fatty acid constituents of phosphatidyl inositol include fatty acids with a saturated or unsaturated linear hydrocarbon chain.

Any pharmaceutically acceptable salt of phosphatidyl inositol (B) may be used, examples of which include salts of alkali metals such as sodium, potassium and lithium; salts of alkaline earth metals such as calcium and magnesium; and salts of inorganic bases such as ammonium.

Either chemically synthesized or naturally occurring phosphatidyl inositol or a salt thereof (B) may be used.

There are known methods including, for example, an enzymatic and chemical synthesis process through an intermediate of arachidonic acid-linking phosphatidic acid (Mori, Scientific report of the Faculty of Agriculture, Okayama University, 9, 2001), and extraction from baker's yeast (Trevelyan, J Lipid Res, 445, 1996).

Commercial products may also be used.

For the mouthfeel and manufacturability of the supplement, the content of phosphatidyl inositol or the salt thereof (B) in the solid supplement is preferably 0.02% or more, more preferably 0.05% or more, even more preferably 0.1% or more, even more preferably 0.2% or more, even more preferably 0.3% or more; and for flavor, is preferably 10% or less, more preferably 7% or less, even more preferably 5% or less, even more preferably 4% or less. Hence, the content ranges preferably from 0.02 to 10%, more preferably from 0.05 to 7%, even more preferably from 0.1 to 5%, even more preferably from 0.2 to 4%. In the present invention, the content of phosphatidyl inositol or the salt thereof (B) is expressed in terms of phosphatidyl inositol content.

The content of phosphatidyl inositol or the salt thereof (B) in the solid supplement can be determined by extraction and thin-layer chromatography similar to those for sphingomyelin.

In the solid supplement according to the present invention, the mass ratio of the content of phosphatidyl inositol or the salt thereof (B) in terms of phosphatidyl inositol content to the content of sphingomyelin (A) in the solid supplement, i.e., [(B)/(A)], is from 0.05 to 3; but for the mouthfeel and flavor of the supplement, is preferably 0.07 or more, more preferably 0.1 or more, even more preferably 0.2 or more; and for flavor, is preferably 1.6 or less, more preferably 1.2 or less, even more preferably 0.8 or less. Hence, the mass ratio ranges preferably from 0.07 to 1.6, more preferably from 0.1 to 1.2, more preferably from 0.2 to 0.8.

The solid supplement according to the present invention may suitably contain, in addition to the above-described components, a mineral (e.g., iron, zinc, chromium, selenium, manganese, molybdenum, copper, iodine, phosphorus, potassium and sodium), a vitamin (e.g., vitamin A, vitamin B1, vitamin B2, vitamin B6, vitamin B12, vitamin C, folic acid and their salts or their esters), a sweetener (e.g., a monosaccharide, an oligosaccharide and a synthetic sweetener), an acidulant (e.g., citric acid, malic acid, tartaric acid, lactic acid, succinic acid, adipic acid, glucono-delta-lactone, gluconic acid, acetic acid and fumaric acid), a fragrance, a colorant, a preservative and the like in such an amount that the effects of the present invention is not compromised.

In manufacture of the solid supplement according to the present invention, an acceptable carrier may be added to the formulation as required. Among them, addition of (C) an excipient is preferred for manufacturability.

Examples of the excipient (C) include organic or inorganic excipients: the organic excipients including, for example, sugars such as lactose, starches, sucrose, maltose, glucose and microcrystalline cellulose; and sugar alcohols such as maltitol, reduced maltose syrup, reduced maltose syrup powder, erythritol, xylitol, sorbitol, mannitol, lactitol, trehalose and hydrogenated palatinose, and the inorganic excipients including, for example, sodium chloride, aluminum silicate, calcium silicate, silicon dioxide, light anhydrous silicic acid, calcium sulfate and calcium hydrogen phosphate. Among these, for the mouthfeel, flavor, ease of chewing and tablet hardness of the supplement, the excipient is preferably an organic excipient, more preferably lactose, a starch and a sugar alcohol, even more preferably a sugar alcohol, more preferably maltitol, erythritol and xylitol, even more preferably maltitol. Those may be used singly or in combination. The sugar alcohol may be either anhydrous or hydrated.

For manufacturability, the content of the excipient (C) in the solid supplement is preferably 25% or more, more preferably 35% or more, even more preferably 40% or more; and in order to add an active ingredient, is preferably 99.8% or less, more preferably 95% or less, even more preferably 90% or less. Hence, the content ranges preferably from 25 to 99.8%, more preferably from 35 to 95%, even more preferably from 40 to 90%.

For the mouthfeel of the supplement, the content of the sugar alcohol in the excipient (C) is preferably 3% or more, more preferably 5% or more, even more preferably 8% or more; and for ease of chewing and tablet hardness, is preferably 75% or less, more preferably 60% or less, even more preferably 50% or less. Hence, the content ranges preferably from 3 to 75%, more preferably from 5 to 60%, even more preferably from 8 to 50%.

Furthermore, for mouthfeel, the content of the sugar alcohol (C) in the solid supplement is preferably 2% or more, more preferably 4% or more, even more preferably 8% or more; and for ease of chewing and tablet hardness, is preferably 70% or less, more preferably 55% or less, even more preferably 45% or less. Hence, the content ranges preferably from 2 to 70%, more preferably from 4 to 55%, even more preferably from 8 to 45%.

HPLC may be used for quantitation of the sugar alcohol. The analysis may be carried out, for example, by differential refractometry using an amino based column (SHOKUMOTSU SENI KISO TO OUYOU (an English translation of the Japanese title: "Dietary Fiber—Basics and Applications") supervised by the Japanese Association for Dietary Fiber Research, edited by the editorial committee of the Japanese Association for Dietary Fiber Research et al., written by Seiichiro Aoki, published by DAI-ICHI SHUPPAN Co. Ltd., on October 2008).

Examples of other additives which are added during manufacture of the solid supplement as required include carriers such as binders (e.g., hydroxypropyl methylcellulose, hydroxypropyl cellulose, gelatin, gelatinized starch, polyvinylpyrrolidone, polyvinyl alcohol, pullulan methylcellulose and hydrogenated oil), disintegrants (e.g., carmellose, carmellose calcium, croscarmellose sodium, crospovidone, corn starch and low substituted hydroxypropyl cellulose), flavors (e.g., stevia), such as extenders, surfactants, dispersing agents, buffers, preservatives and diluents.

To the solid supplement according to the present invention may also be added a lubricant other than phosphatidyl inositol or a salt thereof. Examples of such lubricants include calcium stearate, magnesium stearate, sodium stearyl fumarate, sucrose fatty acid esters, talc and silicon dioxide.

The form of the solid supplement according to the present invention is not particularly limited as long as it remains solid at room temperature (15 to 25° C.) Examples of dosage form of the solid supplement include tablets and troches. Among them, chewable tablets and troches are preferred because of their ease of consumption, and chewable tablets are more preferred. When the supplement is formulated into a tablet, it may also be made into a scored one.

The solid supplement can take form of a circular tablet or a tablet of irregular shape such as a planar oval, a planar ellipse and a planar rectangle. In the case of the circular tablet, a diameter of 5 to 15 mm is preferred for consumption.

If the solid supplement according to the present invention is a tablet, the weight per tablet is preferably from 0.1 to 2 g, more preferably from 0.3 to 1 g for convenience and effectiveness.

The tablet hardness is preferably high enough to enable the tablet to withstand delivery, storage, loads during its release from a fully-automatic tablet packaging machine or from a press-through packaging (PTP) machine for medicines, etc. The tablet hardness is therefore preferably from 30 to 140 N, more preferably from 40 to 90 N.

The solid supplement according to the present invention is manufactured by conventional technique without particular limitation. For example, it can be manufactured by preparing the mixture of sphingomyelin (A), phosphatidyl inositol or the salt thereof (B) and optionally an additive which is added as required, and then compression-molding the mixture. The tablet may be formed by compression-molding the above mixture directly (direct powder compression), or by first granulating the mixture through dry granulation, wet granulation or the like, and then compression-molding the resulting granulate (granulation and compression technique). Among those techniques, tableting by direct powder compression is preferred because of its convenient step.

When the tablet is manufactured by direct compression-molding, a press conventionally used as a tablet molding press can be used, such as a rotary tablet press and a single punch tablet press.

In the case of tableting by first granulating through a granulation technique, a granulate is produced by extrusion granulation using a basket granulator, spheronizing equipment, a pelleter or the like; crushing granulation using a speed mill, a power mill or the like; rolling granulation; stirring granulation; fluid-bed granulation; or the like, and the resulting granulate can be dried, sized, and finally compressed by the above-described tablet molding press to form the tablet. The granulate preferably has a particle size of from 45 μm to 850 μm, more preferably from 100 μm to 500 μm.

The pressure during compression molding in the tableting process is preferably from about 10 to about 30 MPa for reasons of maintaining the hardness, achieving disintegration properties of the molded products and the like.

Aspects and preferred embodiments of the present invention are illustrated below.

<1> A solid supplement comprising the following components (A) and (B):
(A) a sphingomyelin in an amount of from 0.15 to 7% by mass; and
(B) a phosphatidyl inositol or a salt thereof, wherein the mass ratio of the content of phosphatidyl inositol or the salt thereof (B) in terms of phosphatidyl inositol content to the content of sphingomyelin (A) in the solid supplement, i.e., [(B)/(A)], is from 0.05 to 3.

<2> The solid supplement according to <1>, wherein the content of sphingomyelin (A) in the solid supplement is preferably 0.2% by mass or more, more preferably 0.3% by mass or more, even more preferably 0.5% by mass or more; preferably 6% by mass or less, more preferably 5% by mass or less, even more preferably 3% by mass or less; and preferably from 0.2 to 6% by mass, more preferably from 0.3 to 5% by mass, even more preferably from 0.5 to 3% by mass.

<3> The solid supplement according to <1> or <2>, wherein the content of phosphatidyl inositol or the salt thereof (B) in terms of phosphatidyl inositol content in the solid supplement is preferably 0.02% by mass or more, more preferably 0.05% by mass or more, more preferably 0.1% by mass or more, even more preferably 0.2% by mass or more, even more preferably 0.3% by mass or more; preferably 10% by mass or less, more preferably 7% by mass or less, even more preferably 5% by mass or less, even more preferably 4% by mass or less; and preferably from 0.02 to 10% by mass, more preferably from 0.05 to 7% by mass, even more preferably from 0.1 to 5% by mass, even more preferably from 0.2 to 4% by mass.

<4> The solid supplement according to any one of <1> to <3>, wherein the mass ratio of the content of phosphatidyl inositol or the salt thereof (B) in terms of phosphatidyl inositol content to the content of sphingomyelin (A) in the solid supplement is preferably 0.07 or more, more preferably 0.1 or more, even more preferably 0.2 or more; preferably 1.6 or less, more preferably 1.2 or less, even more preferably 0.8 or less; and preferably from 0.07 to 1.6, more preferably from 0.1 to 1.2, even more preferably from 0.2 to 0.8.

<5> The solid supplement according to any one of <1> to <4>, wherein palmitic acid in the total fatty acid constituents of sphingomyelin (A) is preferably 50% by mass or less, more preferably 40% by mass or less, even more preferably 30% by mass or less, even more preferably 20% by mass or less; preferably 1% by mass or more, more preferably 2% by mass or more, even more preferably 5% by mass or more, even more preferably 10% by mass or more; and preferably from 1 to 50% by mass, more preferably from 2 to 40% by mass, even more preferably from 3 to 30% by mass, even more preferably from 5 to 20% by mass, even more preferably from 10 to 20% by mass.

<6> The solid supplement according to any one of <1> to <5>, preferably comprising (C) an excipient.

<7> The solid supplement according to <6>, wherein the content of the excipient (C) in the solid supplement is preferably 25% by mass or more, more preferably 35% by mass or more, even more preferably 40% by mass or more; preferably 99.8% by mass or less, more preferably 95% by mass or less, even more preferably 90% by mass or less; and preferably from 25 to 99.8% by mass, more preferably from 35 to 95% by mass, even more preferably from 40 to 90% by mass.

<8> The solid supplement according to <6> or <7>, wherein the excipient (C) preferably comprises an organic excipient, more preferably one or more selected from the group consisting of lactose, a starch and a sugar alcohol, more preferably a sugar alcohol, even more preferably one or more selected from the group consisting of maltitol, erythritol and xylitol.

<9> The solid supplement according to <8>, wherein the content of the sugar alcohol in the excipient (C) is preferably 3% by mass or more, more preferably 5% by mass or more, even more preferably 8% by mass or more; preferably 75% by mass or less, more preferably 60% by mass or less, even more preferably 50% by mass or less; and preferably from 3 to 75% by mass, more preferably from 5 to 60% by mass, even more preferably from 8 to 50% by mass.

<10> The solid supplement according to <8> or <9>, wherein the content of the sugar alcohol (C) in the solid supplement is preferably 2% by mass or more, more preferably 4% by mass or more, even more preferably 8% by mass or more; preferably 70% by mass or less, more preferably 55% by mass or less, even more preferably 45% by mass or less; and preferably from 2 to 70% by mass, more preferably from 4 to 55% by mass, even more preferably from 8 to 45% by mass.

<11> The solid supplement according to any one of <1> to <10>, wherein the solid supplement is preferably a tablet or a troche, more preferably a chewable tablet or a troche, and more preferably a chewable tablet.

<12> The solid supplement according to any one of <1> to <11>, wherein the solid supplement preferably takes form of a circular tablet or a tablet of irregular shape of a planar oval, a planar ellipse and a planar rectangle.

<13> The solid supplement according to any one of <1> to <12>, wherein the weight per tablet, when the solid supplement is a tablet, is preferably from 0.1 to 2 g, more preferably from 0.3 to 1 g.

<14> The solid supplement according to any one of <1> to <13>, wherein the tablet hardness, when the solid supplement is a tablet, is preferably from 30 to 140 N, more preferably from 40 to 90 N.

<15> A method for preventing tableting problems with a solid supplement comprising sphingomyelin, wherein the method comprises adding phosphatidyl inositol or the salt thereof (B) to the solid supplement comprising sphingomyelin (A).

<16> A method for preventing a solid supplement comprising sphingomyelin from sticking and capping, wherein the method comprises adding phosphatidyl inositol or the salt thereof (B) to the solid supplement comprising sphingomyelin (A).

<17> The method according to <15> or <16>, wherein the mass ratio of the content of phosphatidyl inositol or the salt thereof (B) in terms of phosphatidyl inositol content to the content of sphingomyelin (A) in the solid supplement, i.e., [(B)/(A)], is from 0.05 to 3.

EXAMPLES

Raw Materials

Sphingomyelin (SM): COATSOME NM-70 manufactured by NOF CORPORATION, with palmitic acid of around 16% by mass in the total fatty acid constituents.

Phosphatidyl inositol (PI): L-alpha-Phosphatidylinositol sodium salt manufactured by Sigma-Aldrich Corporation.

Sucrose fatty acid ester: Ryoto Sugar Ester B-370F manufactured by Mitsubishi-Kagaku Foods Corporation.

Calcium stearate: AULABRITE CA-65 manufactured by NOF CORPORATION.

Talc: manufactured by Wako Pure Chemical Industries, Ltd.

Lactose: manufactured by Laprino Foods.

Starch: native tapioca manufactured by Matsutani Chemical Industry Co., Ltd.

Cellulose: KC FLOCK W400-G manufactured by NIPPON PAPER INDUSTRIES CO., LTD. CHEMICAL DIVISION.

Maltitol: Amalty MR-100 manufactured by Mitsubishi Shoji Foodtech Co., Ltd.

Erythritol: manufactured by Mitsubishi-Kagaku Foods Corporation.

Xylitol: manufactured by B Food Science Co., Ltd.

Examples 1 to 9 and Comparative Examples 1 to 6

Manufacture of Tablets

SM, PI, talc and lactose, ground in a mortar, were used. Each raw material was passed through a 50-mesh screen, and those raw material components were then mixed together in accordance with the composition described in Table 1. Circular tablets, each of 500 mg weight, were then produced using a hydraulic tablet press (RIKEN CD-10) with the punches having a diameter of 13 mm at a tableting pressure of 20 MPa.

The above-obtained products according to the present invention and comparative products were evaluated in the following way. The evaluations were made by a panel of five experts in sensory evaluation of food, and each evaluation score was obtained by averaging the evaluations made by the panel. The results are shown in Table 1.

Tabletability

The appearance of the tablets was evaluated by visual inspection based on the evaluation criteria shown below. Sticking refers to an event in which when adhesion between a tablet surface and a punch upon tableting is stronger than the structural integrity of the tablet, a portion of the tablet surface is adhered to the punch surface to leave defects on the tablet surface. Capping refers to an event in which air, once trapped within a tablet upon pressing, is pushed and confined into the upper circumferential portion in the tablet, causing detachment of the upper side from the tablet in a cap-form.

5: excellent, without occurrence of sticking, capping or non-uniformity of color 4: good, with few occurrence of sticking, capping or non-uniformity of color 3: relatively good, with sparse occurrence of sticking, capping or non-uniformity of color 2: relatively poor, with occurrence of sticking, capping or non-uniformity of color 1: poor, with significant occurrences of sticking, capping or non-uniformity of color Mouthfeel The mouthfeel of the tablets when put in the mouth was evaluated based on the evaluation criteria shown below.

5: good, very smooth
4: good, smooth
3: relatively good, relatively smooth
2: relatively poor, relatively rough
1: poor, rough Intensity of Oily Smell The smell of the tablets was evaluated based on the evaluation criteria shown below.

5: no oily smell
4: an oily smell barely recognizable
3: some oily smell
2: a strong oily smell
1: a very strong oily smell following way. [Tabletability], [Mouthfeel] and [Intensity of Oily Smell] were evaluated on the above-described criteria. The evaluations were made by a panel of five experts in sensory evaluation of food, and each evaluation score was obtained by averaging the evaluations made by the panel.

TABLE 1

| | | | | | (% by mass) | | | | |
|---|---|---|---|---|---|---|---|---|---|
| | Example 1 | Example 2 | Example 3 | Example 4 | Example 5 | Example 6 | Example 7 | Example 8 | Example 9 |
| (A) SM | 1.5 | 1.5 | 1.5 | 1.5 | 1.5 | 0.2 | 0.5 | 2.5 | 5 |
| (B) PI | 0.1 | 0.3 | 0.6 | 1.2 | 2.4 | 0.12 | 0.3 | 1.5 | 3 |
| Sucrose fatty acid esters | — | — | — | — | — | — | — | — | — |
| Calcium stearate | — | — | — | — | — | — | — | — | — |
| Talc | — | — | — | — | — | — | — | — | — |
| Lactose | 72.6 | 72.6 | 72.6 | 72.6 | 72.6 | 72.6 | 72.6 | 72.6 | 72.6 |
| Starch | 20.8 | 20.6 | 20.3 | 19.7 | 18.5 | 22.08 | 21.6 | 18.4 | 14.4 |
| Cellulose | 5 | 5 | 5 | 5 | 5 | 5 | 5 | 5 | 5 |
| Total | 100.0 | 100.0 | 100.0 | 100.0 | 100.0 | 100.0 | 100.0 | 100.0 | 100.0 |
| Mass ratio (B)/(A) | 0.07 | 0.2 | 0.4 | 0.8 | 1.6 | 0.6 | 0.6 | 0.6 | 0.6 |
| Evaluation Tabletability | 3.4 | 3.8 | 4.0 | 4.2 | 3.4 | 3.2 | 3.6 | 4.0 | 3.4 |
| Mouthfeel | 3.2 | 3.4 | 4.0 | 4.0 | 4.2 | 3.0 | 3.6 | 4.2 | 4.2 |
| Intensity of oily smell | 4.8 | 4.2 | 4.0 | 3.6 | 3.2 | 4.4 | 4.2 | 3.6 | 3.0 |

| | (% by mass) | | | | | |
|---|---|---|---|---|---|---|
| | Comparative Example 1 | Comparative Example 2 | Comparative Example 3 | Comparative Example 4 | Comparative Example 5 | Comparative Example 6 |
| (A) SM | 1.5 | 1.5 | 1.5 | 1.5 | 1.5 | 7.5 |
| (B) PI | — | — | — | — | 4.8 | 4.5 |
| Sucrose fatty acid esters | — | 0.1 | — | — | — | — |
| Calcium stearate | — | — | 0.1 | — | — | — |
| Talc | — | — | — | 0.1 | — | — |
| Lactose | 72.6 | 72.6 | 72.6 | 72.6 | 72.6 | 72.6 |
| Starch | 20.9 | 20.8 | 20.8 | 20.8 | 16.1 | 10.4 |
| Cellulose | 5 | 5 | 5 | 5 | 5 | 5 |
| Total | 100.0 | 100.0 | 100.0 | 100.0 | 100.0 | 100.0 |
| Mass ratio (B)/(A) | — | — | — | — | 3.2 | 0.6 |
| Evaluation Tabletability | 2.4 | 3.2 | 3.2 | 3.0 | 3.0 | 3.0 |
| Mouthfeel | 1.8 | 2.6 | 2.4 | 2.0 | 4.2 | 4.2 |
| Intensity of oily smell | 4.8 | 4.0 | 4.0 | 4.4 | 2.2 | 2.2 |

As apparent from Table 1, Examples 1 to 9 comprising certain amounts of phosphatidyl inositol exhibited good tabletability, smoothness, good mouthfeel, a faint oily smell and good flavor. On the other hand, Comparative Example 1 lacking a lubricant exhibited poor tabletability and a rough texture, and Comparative Examples 2 to 4, each comprising a lubricant other than phosphatidyl inositol, exhibited a rough texture. Furthermore, Comparative Example 5 with a high ratio of phosphatidyl inositol to sphingomyelin and Comparative Example 6 comprising a high content of sphingomyelin exhibited a strong oily smell.

Examples 10 to 13 and Comparative Example 7

Manufacture of Tablets

SM, PI and lactose, ground in a mortar, were used. Circular chewable tablets were obtained in the same manner as in Example 1, except that the raw material components were mixed together in accordance with the composition described in Table 2 after each raw material was passed through a 50-mesh screen.

The above-obtained products according to the present invention and comparative product were evaluated in the The tablet hardnesses were also determined. The results are shown in Table 2.

Ease of Chewing

The ease of chewing the tablets when put in the mouth and chewed was evaluated based on the evaluation criteria shown below.
5: excellent, because of hardness suitable for very easy chewing
4: good, because of hardness suitable for easy chewing
3: relatively good, because of hardness slightly difficult for easy chewing
2: relatively poor, because of being too hard or too soft
1: poor, because of being too much hard or too much soft Hardness Immediately after manufacturing, the tablet hardness in the diameter direction was determined using a FUJIWARA HARDNESS TESTER (manufactured by Fujiwara Scientific Co., Ltd.). Each test was performed on two tablets, and the tablet hardness was obtained by averaging the two measurements.

TABLE 2

| | | Example 2 | Example 10 | Example 11 | Example 12 | Example 13 | Comparative Example 7 |
|---|---|---|---|---|---|---|---|
| | | (% by mass) | | | | | |
| (A) SM | | 1.5 | 1.5 | 1.5 | 1.5 | 1.5 | 1.5 |
| (B) PI | | 0.3 | 0.3 | 0.3 | 0.3 | 0.3 | — |
| Lactose | | 72.6 | 67.6 | 22.6 | 67.6 | 67.6 | 67.6 |
| Starch | | 20.6 | 20.6 | 20.6 | 20.6 | 20.6 | 20.9 |
| Maltitol | | 0 | 5 | 50 | 0 | 0 | 5 |
| Erythritol | | 0 | 0 | 0 | 5 | 0 | 0 |
| Xylitol | | 0 | 0 | 0 | 0 | 5 | 0 |
| Cellulose | | 5 | 5 | 5 | 5 | 5 | 5 |
| Total | | 100.0 | 100.0 | 100.0 | 100.0 | 100.0 | 100.0 |
| Mass ratio (B)/(A) | | 0.2 | 0.2 | 0.2 | 0.2 | 0.2 | — |
| Evaluation | Tabletability | 3.8 | 3.6 | 3.0 | 3.6 | 3.6 | 2.8 |
| | Mouthfeel | 3.4 | 4.4 | 4.6 | 4.4 | 4.4 | 2.8 |
| | Intensity of oily smell | 4.2 | 4.2 | 4.2 | 4.2 | 4.2 | 4.4 |
| | Ease of Chewing | 2.6 | 4.6 | 3.2 | 4.8 | 4.6 | 4.4 |
| | Hardness (N) | 23.2 | 59 | 139 | 47.2 | 44.3 | 48.5 |

As apparent from Table 2, Examples 10 to 13 comprising certain amounts of phosphatidyl inositol exhibited good tabletability, smoothness, better mouthfeel, a faint oily smell and good flavor. Furthermore, Examples 10 to 13 exhibited hardness suitable for easy chewing but are still high enough to withstand the processes until consumption such as delivery and storage without damage. On the other hand, Comparative Example 7 lacking phosphatidyl inositol exhibited a rough texture.

The invention claimed is:

1. A solid supplement comprising components (A), (B) and (C):
   (A) sphingomyelin in an amount of from 0.15 to 7% by mass;
   (B) phosphatidyl inositol or a salt thereof; and
   (C) an excipient;
   wherein a mass ratio of a content of phosphatidyl inositol or the salt thereof (B) in terms of phosphatidyl inositol content to a content of sphingomyelin (A) in the solid supplement, [(B)/(A)], is from 0.05 to 3,
   the excipient (C) comprises a sugar alcohol, and
   the solid supplement is a tablet having a hardness of from 30 to 140 N.

2. The solid supplement according to claim 1, wherein the content of phosphatidyl inositol or the salt thereof (B) in terms of phosphatidyl inositol content in the solid supplement is from 0.02 to 10% by mass.

3. The solid supplement according to claim 1, wherein a percentage of palmitic acid in the total fatty acid constituents of sphingomyelin (A) is 50% by mass or less.

4. The solid supplement according to claim 1, wherein a content of the excipient (C) in the solid supplement is from 25 to 99.8% by mass.

5. The solid supplement according to claim 1, wherein the excipient (C) comprises one or more selected from the group consisting of maltitol, erythritol and xylitol.

6. The solid supplement according to claim 5, wherein a content of the one or more selected from the group consisting of maltitol, erythritol and xylitol in the excipient (C) is from 3 to 75% by mass.

7. The solid supplement according to claim 1, wherein the weight per tablet is from 0.1 to 2 g.

8. The solid supplement according to claim 1, wherein the supplement is a chewable tablet or a troche.

9. The solid supplement according to claim 2, wherein a content of the excipient (C) in the solid supplement is from 25 to 99.8% by mass.

10. The solid supplement according to claim 2, wherein the excipient (C) comprises one or more selected from the group consisting of maltitol, erythritol and xylitol.

11. The solid supplement according to claim 10, wherein a content of the one or more selected from the group consisting of maltitol, erythritol and xylitol in the excipient (C) is from 3 to 75% by mass.

12. The solid supplement according to claim 2, wherein the supplement is a tablet and the weight per tablet is from 0.1 to 2 g.

13. The solid supplement according to claim 2, wherein a percentage of palmitic acid in the total fatty acid constituents of sphingomyelin (A) is 50% by mass or less.

14. The solid supplement according to claim 13, wherein a content of the excipient (C) in the solid supplement is from 25 to 99.8% by mass.

15. The solid supplement according to claim 14, wherein the excipient (C) comprises one or more selected from the group consisting of maltitol, erythritol and xylitol.

16. The solid supplement according to claim 15, wherein a content of the one or more selected from the group consisting of maltitol, erythritol and xylitol in the excipient (C) is from 3 to 75% by mass.

17. The solid supplement according to claim 16, wherein the weight per tablet is from 0.1 to 2 g.

18. The solid supplement according to claim 17, wherein the supplement is a chewable tablet or a troche.

19. A solid supplement comprising components (A), (B) and (C):
   (A) sphingomyelin in an amount of from 0.15 to 7% by mass;
   (B) phosphatidyl inositol or a salt thereof; and
   (C) an excipient;
   wherein a mass ratio of a content of phosphatidyl inositol or the salt thereof (B) in terms of phosphatidyl inositol content to a content of sphingomyelin (A) in the solid supplement, [(B)/(A)], is from 0.05 to 3,
   the excipient (C) comprises a sugar alcohol, and
   the solid supplement is a tablet having a hardness of from 30 to 140 N, a tabletability of greater than 2.8, and a mouthfeel of greater than 2.8.

* * * * *